US012026876B2

(12) United States Patent
Hassanpour et al.

(10) Patent No.: US 12,026,876 B2
(45) Date of Patent: Jul. 2, 2024

(54) SYSTEM AND METHOD FOR AUTOMATIC DETECTION OF VERTEBRAL FRACTURES ON IMAGING SCANS USING DEEP NETWORKS

(71) Applicants: The Trustees of Dartmouth College, Hanover, NH (US); Dartmouth-Hitchcock Clinic, Lebanon, NH (US)

(72) Inventors: Saeed Hassanpour, Hanover, NH (US); Yvonne Cheung, Hanover, NH (US); Naofumi Tomita, Hanover, NH (US)

(73) Assignees: The Trustees of Dartmouth College, Hanover, NH (US); Dartmouth-Hitchcock Clinic, Lebanon, NH (US)

(*) Notice: Subject to any disclaimer, the term of this patent is extended or adjusted under 35 U.S.C. 154(b) by 338 days.

(21) Appl. No.: 17/432,847

(22) PCT Filed: Feb. 21, 2020

(86) PCT No.: PCT/US2020/019271
§ 371 (c)(1),
(2) Date: Aug. 20, 2021

(87) PCT Pub. No.: WO2020/172558
PCT Pub. Date: Aug. 27, 2020

(65) Prior Publication Data
US 2022/0148164 A1    May 12, 2022

Related U.S. Application Data

(60) Provisional application No. 62/808,719, filed on Feb. 21, 2019.

(51) Int. Cl.
*G06T 7/00* (2017.01)
*G16H 30/20* (2018.01)

(52) U.S. Cl.
CPC ............ *G06T 7/0012* (2013.01); *G16H 30/20* (2018.01); *G06T 2207/10081* (2013.01);
(Continued)

(58) Field of Classification Search
CPC ....... G06T 7/0012; G16H 50/20; G16H 40/30
See application file for complete search history.

(56) References Cited

U.S. PATENT DOCUMENTS 11,769,250 B2 * 9/2023 Fukuda .................. A61B 5/746
                                                          382/128
2009/0169087 A1   7/2009 Doi
(Continued)

FOREIGN PATENT DOCUMENTS

WO    2016013004    1/2016

OTHER PUBLICATIONS

Tomita, Yuvonne, Saeed, Deep neural networks for automatic detection of osteoporotic vertebral features on CT scans, 2018, Elsevier (Year: 2018).*
(Continued)

*Primary Examiner* — Kevin Ky
(74) *Attorney, Agent, or Firm* — Loginov & Associates, PLLC; William A. Loginov

(57) ABSTRACT

This invention provides systems and methods that can detect incidental OVFs in CT examinations at the level of practicing radiologists. The OVF detection system leverages a deep convolutional neural network (CNN) to extract radiological features from each CT scan slice. These extracted features are processed through a feature aggregation module to make the final diagnosis for the full CT scan. Feature aggregation, can be performed in a variety of ways, including the use of a long short-term memory (LSTM) network. In one example, the CNN can be trained on a predetermined number of CT scans, which are established as reference
(Continued)

standards. This result can effectively the performance of practicing radiologists on this test set in real world clinical circumstances. The system and method can be employed to assist and improve OVF diagnosis in clinical settings by pre-screening routine CT examinations and flagging suspicious cases prior to review by radiologists.

20 Claims, 6 Drawing Sheets

(52) U.S. Cl.
CPC ............... *G06T 2207/20081* (2013.01); *G06T 2207/20084* (2013.01); *G06T 2207/30012* (2013.01)

(56) References Cited

U.S. PATENT DOCUMENTS

| | | | | |
|---|---|---|---|---|
| 2009/0297012 | A1* | 12/2009 | Brett | G06V 10/755 382/128 |
| 2012/0053454 | A1* | 3/2012 | Wang | A61B 6/505 600/425 |
| 2012/0143037 | A1* | 6/2012 | Najarian | A61B 6/032 600/407 |
| 2014/0233820 | A1 | 8/2014 | Wu | |
| 2018/0082443 | A1 | 3/2018 | Risman | |
| 2018/0247020 | A1 | 8/2018 | Itu | |
| 2019/0147125 | A1* | 5/2019 | Yu | G06F 30/20 703/10 |
| 2022/0148164 | A1* | 5/2022 | Hassanpour | A61B 6/5217 |

OTHER PUBLICATIONS

A. Paszke, S. Gross, S. Chintala, Automatic differentiation in PyTorch, 2017, 4 pages.
D.P. Kingma, J. Ba, Adam: a Method for Stochastic Optimization, 2014-2015, 15 pages.
K. He, X. Zhang, S. Ren, and J. Sun, Delving deep into rectifiers: Surpassing human-level performance on imagenet classification, in Proceedings of the IEEE international conference on computer vision, 2015, pp. 1026-1034.
K. He, X. Zhang, S. Ren, J. Sun, Deep residual learning for image recognition, in: 2016 IEEE Conf. Comput. Vis. Pattern Recognit, 2016, 9 pages, https://doi.org/10.1109/CVPR.2016.90.
M.D. Zeiler, R. Fergus, Visualizing and understanding convolutional networks, in: Eur. Conf. Comput. Vis, 2014, pp. 818-833.
P.J. Pickhardt, B.D. Pooler, T. Lauder, A.M. del Rio, R.J. Bruce, N. Binkley, Opportunistic screening for osteoporosis using abdominal computed tomography scans obtained for other indications, Ann. Intern. Med. 158 (2013) 588, https://doi.org/10.7326/0003-4819-158-8-201304160-00003.
R. Tuma, FDA Approves AI-Based Software for Wrist Fracture Detection, May 25, 2018, 1 page.
S. Hochreiter, J. Urgen Schmidhuber, Long Short-Term Memory, Neural Comput. 9 (1997) 1735-1780.
S.J. Lee, P.J. Pickhardt, Opportunistic screening for osteoporosis using body CT scans obtained for other indications: the UW experience, Clin. Rev. Bone Miner. Metabol. 15 (2017) 128-137, https://doi.org/10.1007/s12018-017-9235-7.
Tomita et al., "Deep neural networks for automatic detection of osteoporotic vertebral fractures on CT scans", Computers in Biology and Medicine, vol. 98, doi:10.1016/j.compbiomed.2018.05.011, (Jul. 1, 2018), pp. 8-15, (Apr. 20, 2020), XP085408028.
V. Nair, G.E. Hinton, Rectified linear units improve restricted Boltzmann machines, in: Proc. 27th Int. Conf. Mach. Learn, 2010, 8 pages.

* cited by examiner

SYSTEM AND METHOD FOR AUTOMATIC DETECTION OF VERTEBRAL FRACTURES ON IMAGING SCANS USING DEEP NETWORKS

FIELD OF THE INVENTION

This invention relates to diagnosis and treatment of fractures, and more particularly to the use of computer-aided techniques to detect fractures in vertebra due to (e.g.) osteoporosis.

BACKGROUND OF THE INVENTION

Osteoporotic vertebral fractures (OVFs) are prevalent in older adults and are associated with substantial personal suffering and socio-economic burden. Early diagnosis and treatment of OVFs are critical to prevent further fractures and morbidity. However, OVFs are often under-diagnosed and under-reported in computed tomography (CT) exams as they can be asymptomatic at an early stage. Studies reveal that osteoporosis, a chronic progressive bone disorder related to loss of bone density and quality, affects 10.2 million Americans and 56.2 million people worldwide. The prevalence of OVF is high in older adults, reaching 40% by the age of 80. Weakened bone leads to fragility fractures that are associated with loss of independence and a decrease in the quality of life. If osteoporosis is detected early, it can be effectively treated to reduce future fractures and morbidity. However, before the onset of symptomatic fractures, osteoporosis is frequently silent, resulting in under-diagnosis and under-treatment.

The under-reporting of incidental OVFs in routine CT exams is typically attributed to radiologists' inattention to the sagittal views, the absence of clinical symptoms, and a lack of awareness regarding the clinical importance of asymptomatic OVFs. There are new opportunistic approaches to screen for osteoporosis. See, for example, S. J. Lee, P. J. Pickhardt, *Opportunistic screening for osteoporosis using body CT scans obtained for other indications: the UW experience*, Clin. Rev. Bone Miner. Metabol. 15 (2017) 128-137, https://doi.org/10.1007/s12018-017-9235-7; and P. J. Pickhardt, B. D. Pooler, T. Lauder, A. M. del Rio, R. J. Bruce, N. Binkley, *Opportunistic screening for osteoporosis using abdominal computed tomography scans obtained for other indications*, Ann. Intern. Med. 158 (2013) 588, https://doi.org/10.7326/0003-4819-158-8-201304160-00003, by way of useful background information. These options are opportunistic because they rely on CT examinations performed for indications not related to the spine. As a result, the radiologist could be the first to suspect osteoporosis based on the imaging findings. Furthermore, these new screening approaches are efficient, because they do not require extra imaging time or radiation dose.

It is desirable, therefore to provide a system and method for improved screening of OVFs that takes advantage of CT scan and similar imagery data.

SUMMARY OF THE INVENTION

This invention provides systems and methods that can detect incidental OVFs in chest, abdomen, and pelvis CT examinations at the level of practicing to radiologists. The illustrative OVF detection system leverages a deep convolutional neural network (CNN) to extract radiological features from each slice in a CT scan. These extracted features are processed through a feature aggregation module to make the final diagnosis for the full CT scan. Feature aggregation, can be performed in a variety of ways, including the use of a long short-term memory (LSTM) network. In one example, the CNN can be trained on 1432 CT scans, comprised of 10,546 two-dimensional (2D) images in sagittal view, and can thereby achieve an accuracy of 89.2% and an F1 score of 90.8% based on the evaluation on a held-out test set of 129 CT scans, which are established as reference standards through standard semiquantitative and quantitative methods. This result can effectively the performance of practicing radiologists on this test set in real world clinical circumstances. The system and method can be employed to assist and improve OVF diagnosis in clinical settings by pre-screening routine CT examinations and flagging suspicious cases prior to review by radiologists.

In an illustrative embodiment, a system and method, a system for identifying and diagnosing fractures using a computer processor is provided. A feature extraction module locates fracture-like features in a plurality of images generated by a scanner, which includes a patient's bone structure, based upon training data. A feature aggregation module identifies fracture regions from the features based upon training data, and a user interface module allows display of information related to the fracture regions. Illustratively, the feature extraction module is based upon a CNN, and produces feature vectors. The feature aggregation module can be based upon an LSTM. The LSTM can include an FC and sigmoid process that produces a final result. In an exemplary implementation, the fractures are located in vertebra of the patient and the scanner is a CT scanner generating 2D image slices in a volume. The system and method can be part of an OVF diagnostic procedure and displayed images can be highlighted to show regions of interest.

BRIEF DESCRIPTION OF THE DRAWINGS

The invention description below refers to the accompanying drawings, of which.

DETAILED DESCRIPTION

I. Hardware Overview

Figure 1:
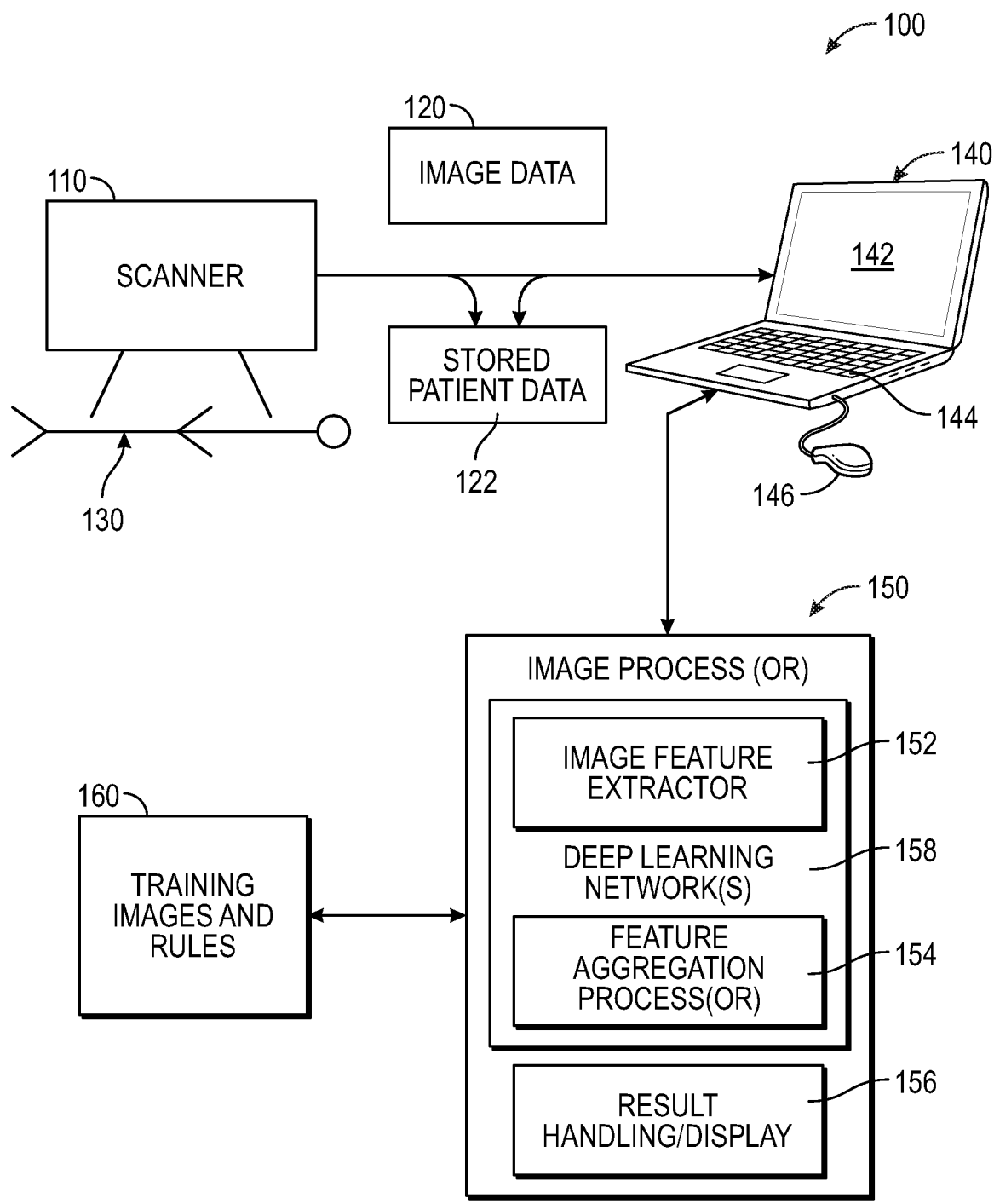
FIG. 1 is a diagram showing an arrangement for acquiring (e.g.) CT scan image data from a patient and performing an OVF detection with a processor having a deep learning network (a convolutional neural network (CNN)) and long short-term memory network (LSTM) instantiated on the processor, according to an exemplary embodiment.

FIG. 1 shows an exemplary arrangement 100 in which a scanner (e.g. a conventional CT scanner) 110 image data 120 in the form of a plurality of slices of the internal anatomy of a patient 130, that collectively provide a 3D image of the patient's scanned region of interest. In this example, the scanned region of interest includes the spine and associated vertebra. The image data 120 is provided to a computing device 140 via a wired or wireless (e.g. WAN or LAN) link, and/or using storage media (e.g. a thumbdrive). More generally, data can be stored in an appropriate form, and can consist of one or more previously conducted scans of the patient. Typically, the scan can be for a purpose other than determining the occurrence of OVFs in the patient (in the thoracic region of the patient in this example). Such stored data can reside on a storage server (e.g. SAN or NAS), cloud computing environment or local hard drive 122 that contains one or more volumes of image scan (e.g. CT) slices. The image data 120 can be represented in a number of forms— for example two-dimensional (2D) pixels or three-dimensional (3D) voxels, and associated metadata with relevant information can be included in the image data 120.

The computing device 140 can be any appropriate, processor based unit, including a PC, laptop, server, tablet, mainframe or cloud computing environment (or combination of such devices). Alternatively, the computing device can be a purpose-built circuitry, such as an FPGA residing, for example, in association with the scanner. In the illustrative example, the computing device includes a graphical user interface (e.g. a display screen or touchscreen 142), with keyboard 144 and mouse, or similar cursor-manipulation device 146. The computing device includes an image process(or) 150 that can be associated with an overall operating system for the device 140. The image processor 150 can include a variety of functional processes and/or modules, including, by way of non-limiting example, an image feature extractor 152 that operates on the image data to retrieve feature information. This can include a trained convolutional neural network (CNN) and/or various conventional or custom components, such as edge detectors, blob tools, trained pattern recognition tools and other tools generally familiar to those of skill. The process(or) 150 can also include a feature aggregation process(or) 154 that generates results from aggregated features based upon (e.g.) a recurrent neural network (RNN). More generally, the results of can be manipulated and displayed using a result handling module 156, which can include various functional blocks for relating data from the network to desired outputs and/or graphical displays that assist the user in understanding the analyzed image data. As described below, the associated deep learning network 158 is trained using various inputs 160, including a plurality of training images related to specific OVF conditions (and/or non-OVF conditions) as described further below.

II. System and Method

By way of further background, it is recognized that recent advancement of machine learning allows automatic diagnosis of various conditions on radiology exams. Such automatic diagnosis has many benefits. For instance, radiologists no longer need to perform the tedious task of screening for incidental findings, and the saved time allows them to interact more with patients and health providers. Furthermore, these automatic diagnostic tools can address the lack of access to expert radiologists in rural, small, or poor communities.

Particularly, embracing machine learning technology for detecting OVFs can improve early diagnosis of osteoporosis, initiate treatment, and predict future fragility fractures. As a result, a successful OVF detection system could potentially decrease the socio-economic burden of osteoporosis. Previous work on automatic OVF detection relied on multiple and fragmented steps on each vertebra. These approaches were inefficient for this detection task because they required vertebra segmentation and calculations of height loss ratio on individual vertebral bodies. An automatic detection system for OVFs was evaluated, based on an end-to-end deep learning model, which does not require multiple segmentation and analysis steps for each vertebra. In the illustrative system and method, a CNN is leveraged to extract radiological features from chest, abdomen, and pelvis CT exams. The resulting sequences of features were then aggregated through a sequence classifier to predict the presence of a vertebral fracture on a CT scan.

Figure 2:
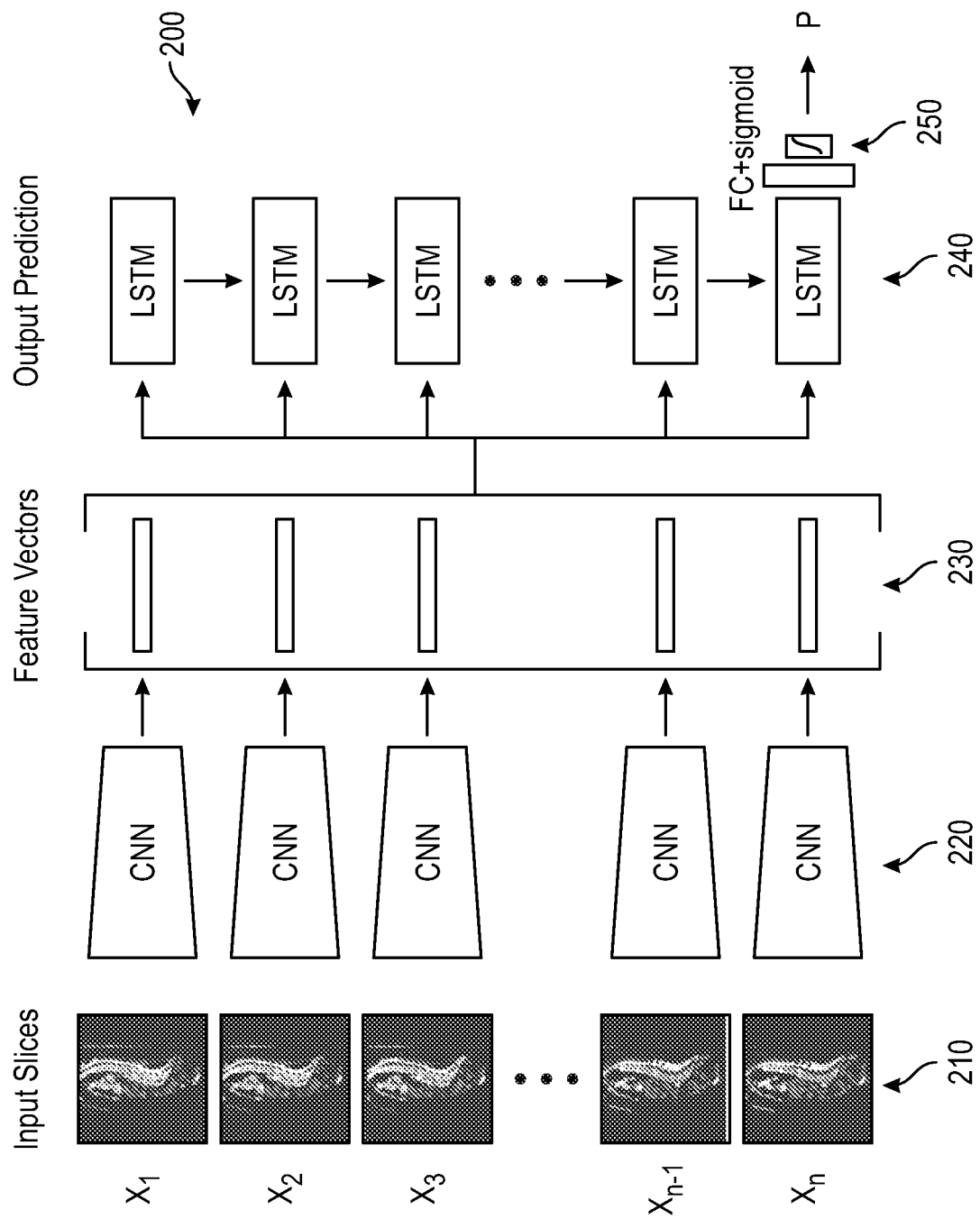
FIG. 2 is a diagram showing an overview of a CNN/LSTM OVF detection system and method operating on the processor of FIG. 1, using the CNN for feature extraction and LSTM for feature aggregation to perform a final patient diagnosis according to an exemplary embodiment.

The illustrative OVF detection system and method can employ a range of different feature aggregation methods using an RNN-based model and three rule-based approaches in combination with a CNN feature extractor. Reference is made to FIG. 2, which shows the overview 200 of an RNN-based OVF detection system used to extract and analyze features from (e.g.) 2D CT scan imagery slices 210. This system has two major components: (1) a CNN-based feature extraction module 220, which generates feature vectors 230; and (2) an RNN module 240 to aggregate the extracted features and make the final patient diagnosis. For processing and extracting features from input two-dimensional (2D) CT slices ($X_1$-$X_n$) 210, the system and method employs a deep residual network (ResNet), which is a current, the state-of-the-art architecture and achieves the most compelling accuracy for image detection. See by way of background, K. He, X. Zhang, S. Ren, J. Sun, *Deep residual learning for image recognition*, in: 2016 IEEE Conf. Comput. Vis. Pattern Recognit, 2016, https://doi.org/10.1109/CVPR.2016.90.

In the illustrative RNN-based feature aggregation, the extracted features from each slice are fed to a long short-term memory (LSTM) network 240. Among different RNN architectures, LSTMs are also currently state-of-the-art and are often utilized to aggregate and analyze temporal or sequential data such as videos or text. See by way of background, S. Hochreiter, J. Urgen Schmidhuber, *LONG SHORT-TERM MEMORY*, Neural Comput. 9 (1997) 1735-1780. LSTM is used to aggregate a flexible number n of slices from a CT scan to make the final diagnosis. In addition to the LSTM-based aggregation method, the system and method can employ three rule-based alternatives for feature aggregation. These rule-based approaches can be directly built into the CNN component and aggregate the confidence scores from each CT slice through (1) taking the maximum, (2) averaging, and (3) voting operations to make the final diagnosis.

It is recognized that an accurate clinical diagnosis requires a set of well-established features that represents a radiology examination. The illustrative system and method essentially replaces the traditional feature extraction process employed by radiologists with a CNN to extract high-level features in 2D CT slices. A CNN with an appropriate capacity of parameters and number of layers can represent characteristic features in complex datasets. The system and method illustratively employs a ResNet architecture with (e.g.) 34 layers (i.e., ResNet34 architecture) to extract features from each slice in a CT scan. The ResNet34 architecture consists of 16 two-layer residual blocks, and a total of 33 convolutional layers and one fully connected (FC) layer.

In experiments, ResNet34 achieved similar results when compared to deeper ResNet architectures with shorter training time. The configuration of this feature extraction network was consistent in all experiments with feature aggregation methods. To adapt this architecture for a binary classification task and to reduce the dimensionality of internal feature representations, the FC layer of the original ResNet34 architecture is replaced with two FC layers, each followed by a batch normalization layer and a rectified linear unit (ReLU) function. By way of background, such a function is described in V. Nair, G. E. Hinton, *Rectified linear units improve restricted Boltzmann machines*, in: Proc. 27th Int. Conf. Mach. Learn, 2010, 10.1.1.165.6419. In operation, the first FC layer reduces the dimensionality of features from 512 to 32, and the second FC layer projects the 32-dimensional vector to a scalar value. This scalar value is normalized by a sigmoid function, $f(x)=1/(1+e^{-x})$, to generate a probability value $\hat{y}\epsilon[0,1]$ as the CNN output. The CNN is trained to make a slice-level classification by minimizing the binary cross-entropy loss between the predicted probability and the reference probability distribution as described below. Here, $y_i$ represents the target label for the i-th slice in a CT scan, and the label of a CT volume is transferred to all its slices.

$$\text{loss}(\hat{y}, y) = -\frac{1}{2}\sum_i (y_i \log(\hat{y}_i) + (1 - y_i)\log(1 - \hat{y}_i))$$

Following feature extraction, the system and method performs feature aggregation. The sequence of features from each CT slice is utilized by the feature aggregation module to make a patient-level diagnosis. Since each CT examination has a different number of slices, the feature aggregator should be able to process an arbitrary number of CT slices. The system and method can employ various approaches to aggregate and classify an arbitrary sequence of feature vectors for a CT scan. The illustrative RNN-based model (CNN/RNN) is a one-layer LSTM network with 256 hidden units followed by an FC layer and a sigmoid layer. The 32-dimensional feature vectors extracted from each CT slice are fed to the network in a sequence, from the first to the last slice. The hidden layer output is a 256-dimensional feature vector. The output at the last slice (p) is used for the final prediction through FC and sigmoid layers 250 (FIG. 2). The final sigmoid layer produces a single normalized value between 0 and 1 as the probability of OVF on a CT scan (this is termed the "confidence score"). In an exemplary embodiment, a threshold of 0.5 can be set for confidence score—this value can be varied via the user interface where desired—for the final binary classification, which is middle point probability threshold to differentiate negative and positive predictions. The rule-based methods herein use slice-level predictions from the last FC layer of the ResNet34 model and aggregate sequential predictions through (1) taking the maximum, (2) averaging, and (3) voting. Given a CT scan with n slices and their corresponding predictions from the last FC layer of ResNet34, $\hat{Y}=|\hat{y}_{i1}, \hat{y}_{i2}, \ldots, \hat{y}_{in}|$, the description of these rule-based aggregation methods are as follows:

CNN/Max: Taking the Maximum 1 if $sup(\hat{Y}_i) > 0.5$, 0 otherwise

CNN/Avg: Averaging 1 if $E(\hat{Y}_i) > 0.5$, 0 otherwise

CNN/Vote: Voting 1 if $\dfrac{\sum_{k=1}^{n} 1_{\hat{y}_{ik}>0.5}}{n} > \theta$, 0 otherwise Where sup(x) and E(x) are the supremum function and expected value, respectively, $\theta$ is a threshold $\in[1,0]$; and $1_{\hat{y}_{ik}\geq 0.5}$ is an indicator function, which returns a value of "1" if the confidence score for the kth slice, $\hat{y}_{ik}$, is greater than 0.5, and returns a value of "0" otherwise. The system and method employs the threshold, $\theta=0.5$, which resulted in the highest accuracy on the validation set.

III. Experimental Procedures and Results

The following is a discussion of experimental procedures and results in association with the above-described system and method, which also reflect runtime operation of the system and method on a data set. The experimental procedures are based upon stored CT exams performed at the Dartmouth-Hitchcock Medical Center (DHMC; Lebanon, NH) from Apr. 16, 2008, to Jan. 9, 2017, and stored in a Montage Search and Analytics™ server (Montage Healthcare Solutions, Philadelphia, PA). The Montage search functionality was employed to identify radiology reports to select all CT exams of the chest, abdomen, and pelvis based on exam codes. The advanced search feature in Montage was also employed to select positive and negative cases for OVF in which positive cases were identified by the term "compression fracture", and negative cases were identified by the lack of the term "compression deformity OR compression fracture" in CT radiology reports. This search yielded a large number of cases. Among these negative cases, the same number of cases was randomly selected as in the positive group and matched for age and sex. For these positive and negative cases, the sagittal reformatted images from the Picture Archiving and Communication System (PACS) (Philips iSite PACS v3.6, Philips Healthcare, Best, Netherlands) were transferred to a local encrypted server, while cases with incomplete data and/or artifacts and noise were omitted.

Figure 3:
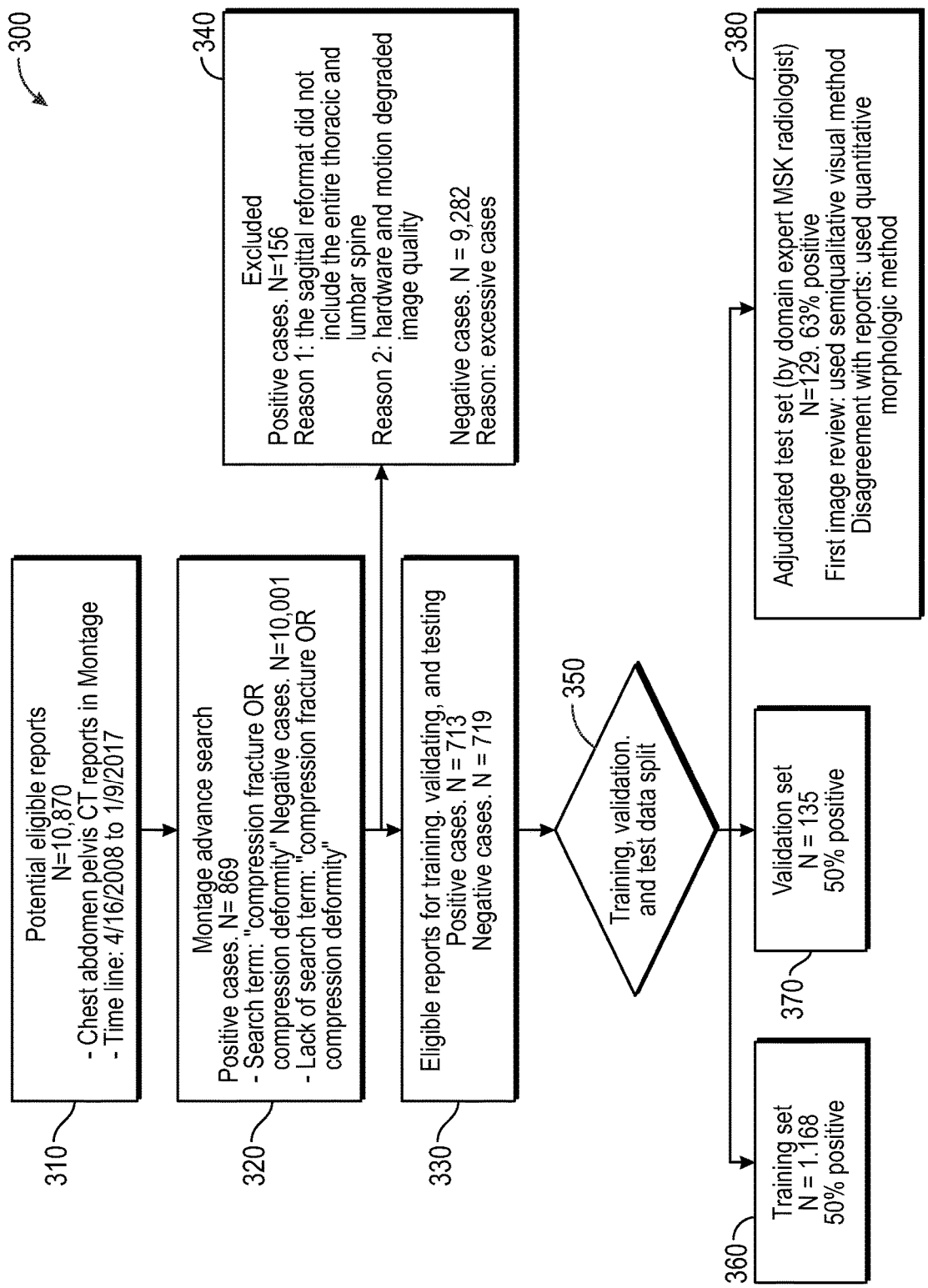
FIG. 3 is a flow diagram showing an overview of the data collection process in an experimental operation of the system and method of FIG. 2 in which the dataset is partitioned into training, validation, and test sets for the development and evaluation of the system and method.
Figure 4A:
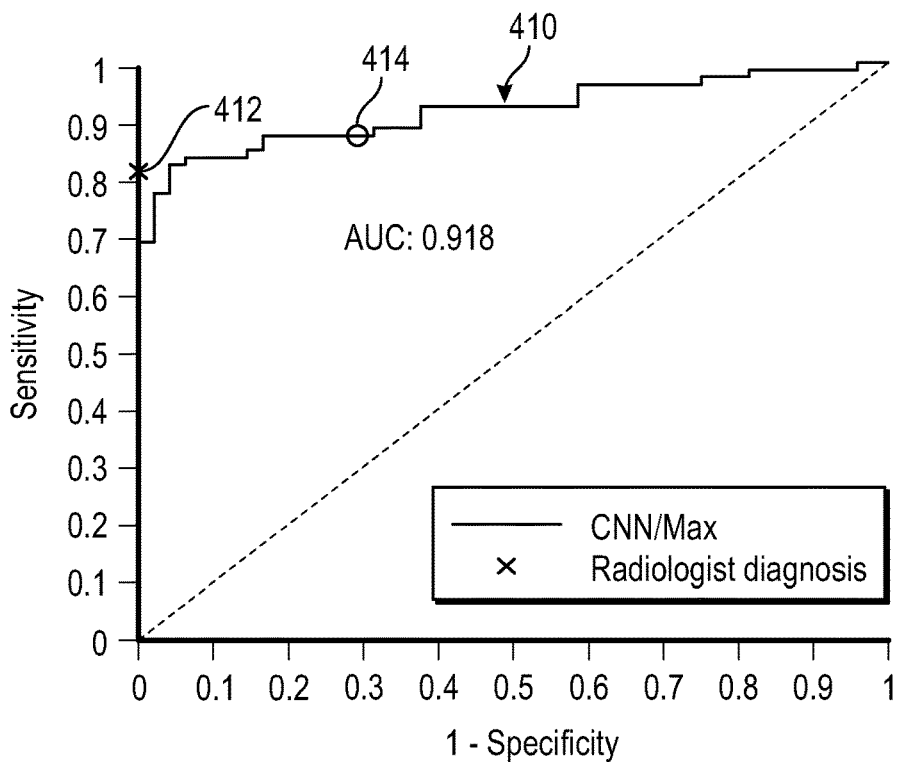
FIGS. 4A-4D are each diagrams of respective ROC curves for the different proposed OVF detection systems on an experimental test set of CT image data, along with the performance of human radiologists and the operating point of the models at a 0.5 threshold.
Figure 4B:
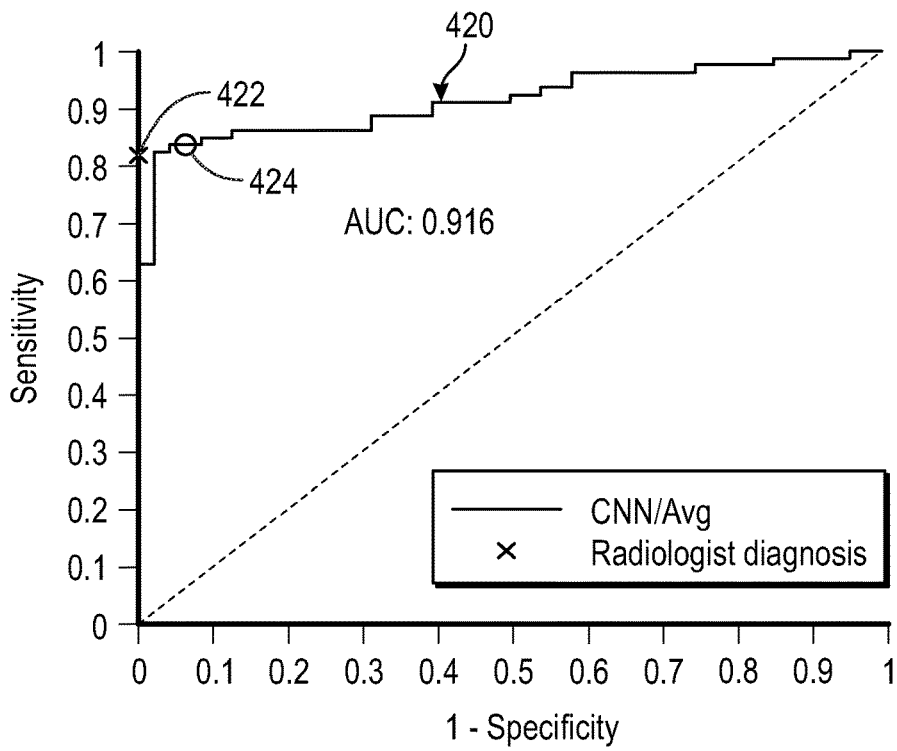
Figure 4C:
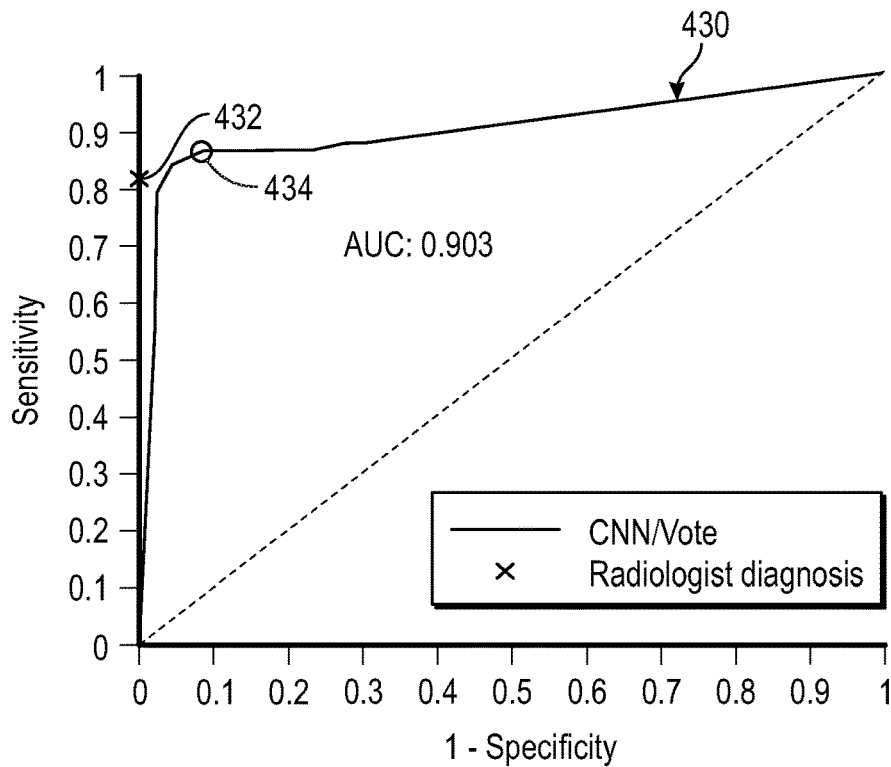
Figure 4D:
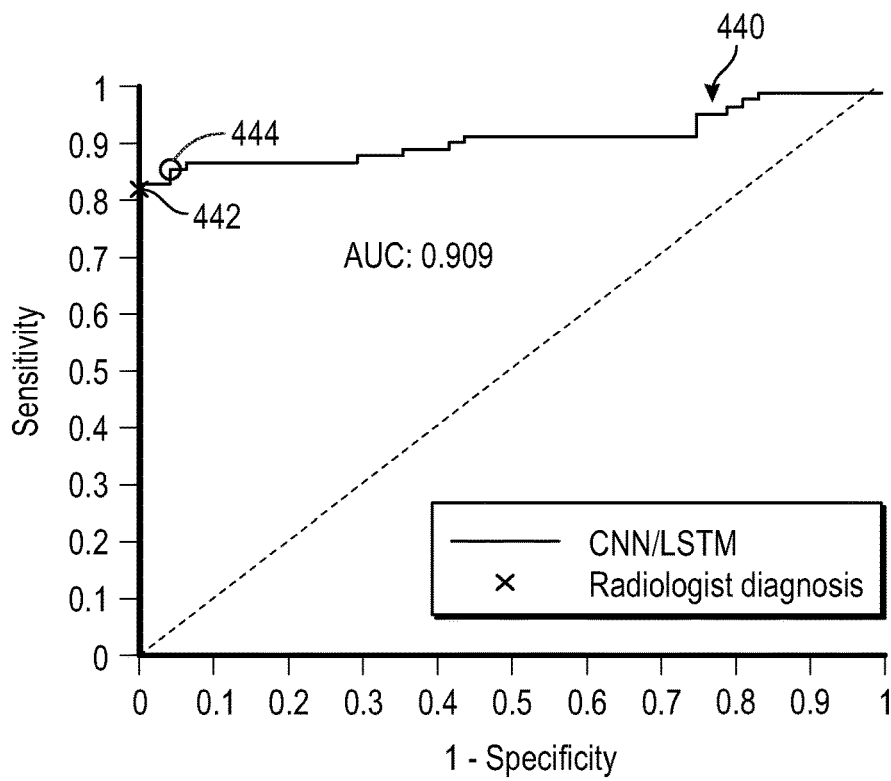

The details of this data extraction process and the number of exams that were included/excluded in each step are shown in the flow diagram 300 of FIG. 3. More particularly, this data extraction process, which started with eligible reports N=10,870 (block 310) was reduced to 1432 CT scans, 713 positive and 719 negative OVF cases (block 330) by advance search tools (block 320) and exclusion (block 340). The procedure randomly split (block 350) the dataset into 80% training (block 360), 10% validation (block 370), and 10% test sets (block 380). This separation is preserved throughout the experiment. The training set is used to train experimental models, while the validation set is used to tune the hyper-parameters for these models. The training and validation sets are labeled according to the positive/negative criteria above, based on radiology reports. Therefore, the training/validation set labels can be prone to errors, due to potential missed diagnosis by radiologists or non-standard reporting, which reflects real-world radiology practice. Using these original labels maximizes the practicality of the system and method's approach, while it may potentially affect the efficacy of the trained model.

The above-described test set is used to evaluate the generalizability of the system and method's approach on unseen CT exams. To evaluate the performance of the method on the test set, extra consideration was taken to identify true-label reference standards for the CT exams in the test set. These reference standards were established through a careful domain-expert radiologist semiquantitative and quantitative re-evaluation, which is described in accordance with test set adjudication below.

As described above, in the experimental procedure using the system and method, 713 positive and 719 negative CT scans were employed. Due to differences among patients and CT scanners, the number of slices in a CT scan varies in the overall test dataset; on average, 146.4+/−2.3 slices are in each CT scan. The size of each CT scan slice is 512×512 pixels in a single color channel. These CT scans were converted from digital imaging and communications in medicine (DICOM) format to JPEG2000 format with the compression ratio of 10:1, which is substantially visually lossless. Also, to normalize the intensity values, a pixel-wise, mean subtraction was performed on the CT slices in the dataset. The mean in this normalization was calculated on the training set. The labels of the training examples are location-agnostic: a positive label only indicates the existence of a vertebral fracture on a CT scan without indicating the location of the fracture. Of note, the relevant CT slices to detect vertebral fractures are the ones that contain spinal column anatomy. Through investigation on the training set, it was observed that these relevant slices are mostly composed of the 5% middle slices in a typical chest, abdomen, and pelvis CT scan. Therefore, only the middle 5% of slices of the CT exams were extracted for the experiment. Although this 5% criterion is chosen heuristically through visual inspection of the training set, this criterion is flexible for any CT volume in the sagittal view. This extraction narrows down the focus of the procedure on the slices that are significant for OVF detection, and it also reduces the noise introduced by considering slices not showing any parts of the spinal column. In addition, this approach reduces the amount of computation at training and inferencing by only examining the most relevant portion of data. This data preprocessing can reduce the computational cost of the model dramatically (about 20 times) without affecting its accuracy. After this extraction, each sample CT scan contained 6.9+/−0.1 slices on average. Data augmentation is a desirable preprocessing step for deep convolutional neural networks to achieve a generalizable performance based on the relatively small dataset used in the experimental procedure. The procedure used random rotation (e.g. rotating an image feature in the range of +/−3 degrees) and horizontal translation (e.g. 12 pixels of 0-padding on each side of an image feature, followed by 512×512 random cropping). The procedure included testing of several other augmentation techniques (which can be applied in alternate systems and methods), such as elastic distortions, lens distortions, and random noise addition, but random rotation and horizontal translation was selected as the exclusive technique in the exemplary experimental procedure.

In experimental operation, an augmented CT slice was input to a ResNet34 network whose size of input is a 3×224×224 tensor, with the subsampling of a slice of 1×512×512 into 1×224×224. This operation was then repeated in threefold to replicate red-green-blue (RGB) pixel channels. The exemplary subsampling scheme includes resizing the image to 224×512 and cropping out the central 224×224 patch. Other subsampling schemes can be employed in alternate implementations.

The experimental procedure further entails feature extraction training of the ResNet34 model. More particularly the ResNet34 model employs two FC layers to extract features from slices in CT scans. This model is trained by using the binary cross-entropy loss function and stochastic gradient descent. The second-to-the-last FC layer outputs, 32-dimensional feature vectors, are used as inputs for the subsequent LSTM classifier, while the last FC layer outputs, confidence scores between 0 and 1, are used in the procedure's rule-based methods. Illustratively, a ResNet34 model defined as part of torch-vision in the PyTorch framework is employed for training. By way of background, such is further described in A. Paszke, S. Gross, S. Chintala, PyTorch, 2017. All parameters throughout the training process are initialized according to the techniques described in K. He, X. Zhang, S. Ren, J. Sun, *Delving deep into rectifiers: surpassing human-level performance on imagenet classification*, in: Proc. IEEE Int. Conf. Comput. Vis, 2015, pp. 1026-1034, and the training mini-batches are selected randomly. The initial learning rate is 0.01 for the mini-batch size of 192. This learning rate is reduced in half whenever no improvement in the objective loss on the validation set for 30 epochs is observed. The Adam optimizer with $\beta_1=0.9$, $\beta_2=0.999$, and $\varepsilon=1e-8$ is employ. See D. P. Kingma, J. Ba, Adam: *a Method for Stochastic Optimization*, 2014. In addition to data augmentation, weight decay of 1e-4 is utilized to stabilize the training process. The experimental model is trained for 400 epochs. All parameters for the batch normalization layers are frozen after this training.

In the illustrative experimental operation, training of the ResNet34 feature extraction network is performed on a high-performance computer that was equipped with an NVIDIA Titan XpGPU, an Intel Xeon E5-1650 CPU, and 16 GB of RAM. Other computing/data processing platforms are expressly contemplated, as described above.

The experimental procedure also performs feature aggregation training. Illustratively, a one-layer LSTM is employed, followed by a fully connected layer and a sigmoid layer for the RNN-based aggregation model. This LSTM network has 256 hidden units, which achieved the best performance among models with different configurations (e.g., 64, 128, 256, 512, 1024) in the illustrative experiment. In contrast to the feature extraction network that was trained on individual CT slices, the aggregation network is trained on all extracted slices from the middle portion of a CT scan. As discussed above, with reference to feature aggregation, the confidence score of the last sigmoid layer is used to generate the final diagnosis.

Similar to a feature extraction network, this classifier is implemented in PyTorch. The initial learning rate can be set to 0.1. CT scans are, thus, input to the network one at a time through the feature extraction network during training, with the aforementioned data augmentation transformations applied on all slices. The dropout technique is also applied in the FC layer with p=0.2. In this training, the FC layers of the feature extraction network are also fine-tuned with the learning rate of 1e-4. After 600 epochs of training, the network can be fine-tuned on the combination of training and validation sets with the learning rate of 1e-6 for 50 more epochs.

Rule-based aggregation methods are also implemented within the PyTorch framework to operate on the last layer of the trained feature extraction network as input. As these rule-based methods are deterministic, they do not require additional training or parameter tuning.

recall. The definitions of these evaluation metrics are included in the following Table 1, where TP is the number of true positives, TN is the number of true negatives, FP is the number of false positives, and FN is the number of false negatives in the test set.

TABLE 1

The performance of our models for the detection of OVFs on CT scans in comparison to practicing radiologists on our adjudicated test set.

| Model | Accuracyy (%) (TP + TN)/ (TP + FP + FN + TN) | Precision (%) TP/(TP + FP) | Sensitivity (%) TP/(TP + FN) | Specificity (%) TN/(TN + FP) | F1 score (%) 2TP/ (2 TP + FP + FN) |
|---|---|---|---|---|---|
| Radiologist diagnosis on report | 88.4 (81.5-93.3) | 100.0 (97.2-89.6) | 81.5 (73.6-87.7) | 100.0 (97.2-100) | 89.8 (83.4-94.5) |
| CNN/Max | 81.4 (73.6-87.7) | 83.5 (76.2-89.6) | 87.7 (80.6-92.7) | 70.8 (61.9-78.2) | 85.5 (78.0-90.9) |
| CNN/Avg | 87.6 (80.6-92.7) | 95.8 (91.2-98.7) | 84.0 (76.3-89.6) | 93.7 (88.1-97.3) | 89.5 (82.5-93.9) |
| CNN/Vote | 88.4 (81.5-93.3) | 97.1 (92.3-99.1) | 84.0 (76.2-89.6) | 95.8 (91.2-98.7) | 90.1 (83.4-94.5) |
| CNN/LSTM | 89.2 (82.5-93.9) | 97.2 (92.3-99.1) | 85.2 (78.0-90.9) | 95.8 (91.2-98.7) | 90.8 (84.3-95.1) |

The experimental procedure was subjected to test set adjudication. Thus, to guarantee the quality of the evaluation, the reference standards in the test set are established through two different approaches: (e.g.) a semiquantitative and a quantitative approach. Both of these approaches are routinely used in clinical studies for assessing vertebral fractures. The assessments in this study were performed by a board-certified radiologist (Y.C.), with over 18 years of musculoskeletal (MSK) radiology experience, who was blinded to the original diagnoses reported in radiology reports and the experimental system's results. In the semiquantitative approach, the domain-expert radiologist reviewed the CT exams in the test set and graded the exams based on a visual inspection. In this well-defined semiquantitative criterion, a CT exam is considered positive for OVF, if it is graded 1, 2, or 3.

In cases of disagreements between the semiquantitative assessment and the blinded OVF diagnoses reported in radiology reports or the system's results, additional investigation through a quantitative morphometric approach was performed to establish the reference standard. In this quantitative approach, a human, domain-expert radiologist measured the vertebral body dimensions using PACS-embedded measuring tools. These measurements were used to calculate the height loss ratio of vertebral bodies. The deformity or wedging with ≥20% height loss, which corresponds to grade 1, 2, and 3 in the semiquantitative approach, were considered positive for OVF in the quantitative adjudication. The height loss in the criteria could be anterior, middle, or posterior for a vertebral body. Similar to previous research, it was observed in this two-phase adjudication, in some cases, that the practicing radiologists did not recognize vertebral fractures on a CT scan. Throughout this exemplary adjudication procedure, 16 originally negative cases in the test set were identified as positive for OVF (accounting for 12.4% of the test set).

In experimental operation, the system outputs a probability value (i.e., a confidence score between 0 and 1) as a diagnosis for each CT scan. A predicted value larger than 0.5 (i.e., middle point probability threshold) is considered positive for OVF on a CT scan, while values less than or equal to 0.5 are considered negative. The performance of the system was evaluated through four standard machine learning metrics on the adjudicated test set: accuracy, precision (positive predictive value), sensitivity (recall), specificity, and F1 score, which is the harmonic mean of precision and The results using the system of the exemplary embodiment for detecting OVFs on the adjudicated 129 CT scans in the test set are tabulated generally in Table 1. The performance of the system is also compared to human radiologists' diagnoses as extracted from CT scans' radiology reports in this table. Table 1 shows, among all the proposed models, the CNN/RNN combination achieved the best accuracy and F1 score. Moreover, it is recognized that the accuracy and F1 score of this model matched the human radiologists' performance in detecting OVFs as part of their real-world daily clinical routine.

To further investigate the sensitivity and specificity of the techniques used in the experimental operation of the system, FIGS. 4A, 4B, 4C and 4D respectively show plots 410, 420, 430 and 440 of the Receiver Operating Characteristic (ROC) performance curves (sensitivity versus specificity) for different thresholds between 0 and 1. Plot 410 is based on a CNN/MAX approach, plot 420 is based on CNN/AVG approach, plot 430 is based on CNN/Voting approach and plot 440 is based on a CNN/LSTM approach (the exemplary system herein). Each plot 410, 420, 430 and 440 depicts the respective operating point 414, 424, 434 and 444 of the model at the 0.5 threshold. The performance of the human radiologists 412, 422, 432 and 442 is also provided on these plots. Although the area under the ROC curve (AUC) is depicted as relatively high (>0.9) for all approaches, it can be observed that the ROC for the CNN/LSTM approach (plot 440 in FIG. 4D) overlaps with the human radiologists' performance. These results indicate that the CNN/LSTM approach of the illustrative system and method has high efficacy for diagnosing OVF, and that its performance is on par with practicing radiologists.

Figure 5:
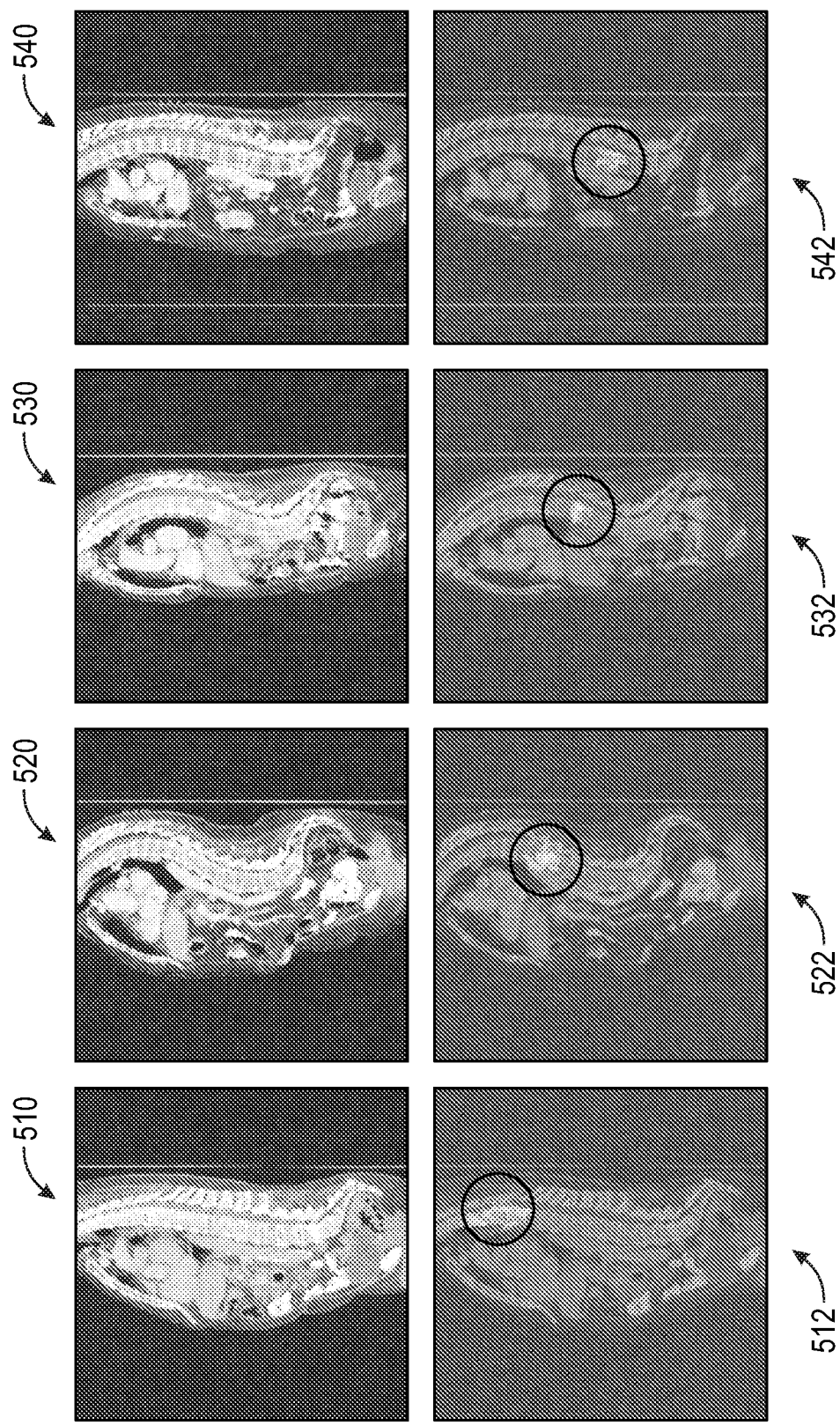
FIG. 5 is a diagram showing an image display of four examples from CTs that were identified positive for OVFs by the CNN/LSTM classification approach of the system and method of FIG. 2, with fractures in thoracic vertebrae and lumbar vertebrae, and associated color maps highlighting respective regions that are strongly associated with these classification outputs in the model of the system and method.

An occlusion visualization technique (See for background M. D. Zeiler, R. Fergus, *Visualizing and understanding convolutional networks*, in: Eur. Conf. Comput. Vis, 2014, pp. 818-833) can be employed to verify that the features used by the illustrative system to identify OVFs on CT scans were actually associated with vertebral fractures. FIG. 5 shows display images 510, 520, 530 and 540 of four examples of this visualization, each representing a CT image that was identified as positive for OVFs by the illustrative CNN/LSTM system. Images 510 and 520 represent fractures in thoracic vertebra, while imaged 530 and 540 represent fractures in lumbar vertebra. The projected color (shown herein as a black and white image) maps 512, 522, 532 and 542 on these images also respectively highlight (the highlight residing within the circled region in each image frame)

the detected fractures on each CT slice. They highlight the regions that are strongly associated with these classification outputs in the model herein. Notably, a version of the depicted the visualization of FIG. 5 can be incorporated as part of a graphical user interface presented to the user in a runtime example of the system and method.

IV. Conclusion

It should be clear that the above-described system and method and associated analytic techniques provides a highly useful and robust technique for identifying and diagnosing OVFs (and other related orthopedic conditions) in patients who have undergone CT and related imagery. This system and method, unlike prior art implementations, advantageously trains and operates the entire system over a unified deep neural network framework, and makes the final diagnosis on CT volumes from the patient's imagery, rather than basing a diagnosis on single CT slices, or small slice patches. Using whole CT volumes for diagnosis is particularly instrumental in cases of patients with deformed spines (e.g., scoliosis). Of note, analysis of each CT scan in the best of the aforementioned models took approximately five minutes to process on a high-performance computer, while the exemplary system and method reduces this time to less than 0.02 second on average for the full analysis of a CT scan, which does not stall the clinical workflow. Therefore, in contrast to the previous methods, the illustrative holistic, deep learning approach of the system and method presents a fast, efficient, and accurate diagnostic tool in this domain. Hence, the exemplary, automatic detection system and method herein can potentially reduce the time and the manual burden on radiologists for OVF screening, as well as reducing the potential false negative errors arising in asymptomatic early stage vertebral fracture diagnoses. This can help to provide better early detection and treatment of osteoporosis, leading to a decrease in the overall socio-economic burden of osteoporosis, and a significant improvement in associated health outcomes. Moreover, this system and method can provide a platform to improve the quality of care for rural, small, and poor communities worldwide, where access to radiology expertise is limited.

V. Related Materials

A research paper by Naofumi Tomita, Yvonne Y. Cheung, and Saeed Hassanpour entitled, *Deep neural networks for automatic detection of osteoporotic vertebral fractures on CT scans*, Computers in Biology and Medicine 98 (2018) 8-15 is available on the World Wide Web at https://www-.sciencedirect.com/science/article/pii/S0010482518301185?via%3Dihub, and which includes reference and other information by way of further useful background herein, and is incorporated by reference.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A system for identifying and diagnosing fractures using a computer processor comprising:
    a feature extraction module that locates fracture-like features in a plurality of images generated by a scanner, which includes a patient's bone structure, based upon training data, wherein the feature extraction module applies a deep residual network to generate and classify feature vectors representative of the fracture-like features based on cross-entropy loss minimization;
    a feature aggregation module that predicts a fracture diagnosis confidence score for fracture regions of the patient's bone structure from the located fracture-like features by processing the feature vectors through a long short-term memory neural network and normalizing a resulting multi-dimensional feature vector as the diagnostic confidence score; and
    a user interface module that allows displays of fracture diagnosis of information related to the fracture regions of the patient's bone structure.

2. The system as set forth in claim 1 wherein the feature extraction module is based upon a CNN and produces feature vectors.

3. The system as set forth in claim 2 wherein the feature aggregation module is based upon an LSTM.

4. The system as set forth in claim 3 wherein a layer of the LSTM includes an FC and sigmoid process that produces a final result.

5. The system as set forth in claim 4 wherein the fractures are located in vertebra of the patient.

6. The system as set forth in claim 5 further comprising a display interface that provides images of the vertebra with highlighted regions of interest shown in at least one of a differing brightness and a differing contrast.

7. The system as set forth in claim 1 wherein the scanner is a CT scanner generating 2D image slices in a volume.

8. The system as set forth in claim 1 wherein the deep residual network comprises 16 two-layer residual blocks.

9. The system as set forth in claim 1 wherein the deep residual network reduces feature dimensionality by a factor of 8.

10. The system as set forth in claim 1 wherein the cross-entropy loss is based on a predicted probability of a classification of a corresponding feature vector and a reference probability distribution thereof.

11. A method for identifying and diagnosing fractures using a computer processor comprising the steps of:
    locating and extracting fracture-like features in a plurality of images generated by a scanner, which includes a patient's bone structure, based upon training data;
    applying a deep residual network to generate and classify feature vectors representative of the fracture-like features based on cross-entropy loss minimization;
    aggregating extracted features and identifying fracture regions based upon training data;
    predicting a fracture diagnosis confidence score for the fracture regions by processing the feature vectors through a long short-term memory neural network and normalizing a resulting multi-dimensional feature vector as the confidence score; and
    displaying fracture diagnosis information related to the fracture regions.

12. The method as set forth in claim 11 wherein the step of locating and extracting is based upon generation of a CNN and producing feature vectors.

13. The method as set forth in claim 12 the step of aggregating is based upon an LSTM.

14. The method as set forth in claim 13 wherein a layer of the LSTM includes an FC and sigmoid process that produces a final result.

15. The method as set forth in claim 14 wherein the fractures are located in vertebra of the patient.

16. The method as set forth in claim 15 further comprising displaying images of the vertebra with highlighted regions of interest shown in at least one of a differing brightness and a differing contrast.

17. The method as set forth in claim 16 wherein the plurality of images are generated using a scanning device generates 2D image slices of a bone structure in a body.

18. The method as set forth in claim 17 wherein the scanner is a CT scanner.

19. The method as set forth in claim 16 wherein the images are employed to assist osteoporotic vertebral fractures (OVF) diagnosis.

20. The method as set forth in claim 11 wherein predicting a fracture diagnosis configence score includes applying three rules when processing the feature vectors including taking a maximum, averaging, and voting therefore.

* * * * *